(12) United States Patent
Romero et al.

(10) Patent No.: US 9,162,048 B2
(45) Date of Patent: *Oct. 20, 2015

(54) SYSTEMS AND METHODS FOR MAKING AND USING TIP ELECTRODES FOR LEADS OF ELECTRICAL STIMULATION SYSTEMS

(71) Applicant: BOSTON SCIENTIFIC NEUROMODULATION CORPORATION, Valencia, CA (US)

(72) Inventors: Daniel James Romero, Newhall, CA (US); William George Orinski, Reno, NV (US); Joshua Dale Howard, North Hollywood, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/265,306

(22) Filed: Apr. 29, 2014

(65) Prior Publication Data

US 2014/0343647 A1    Nov. 20, 2014

Related U.S. Application Data

(60) Provisional application No. 61/823,743, filed on May 15, 2013.

(51) Int. Cl.
*A61N 1/00* (2006.01)
*A61N 1/05* (2006.01)
(Continued)

(52) U.S. Cl.
CPC ............ *A61N 1/05* (2013.01); *A61N 1/0529* (2013.01); *A61N 1/0551* (2013.01);
(Continued)

(58) Field of Classification Search
CPC ..... A61N 1/05; A61N 1/0529; A61N 1/0534; A61N 1/0551; A61N 1/0565; Y10T 29/49117; Y10T 29/49172; Y10T 29/49208; B29C 2045/14122; B29C 70/84

USPC .......................................................... 607/116
See application file for complete search history.

(56) References Cited

U.S. PATENT DOCUMENTS 4,413,636 A    11/1983  Jasso
4,602,624 A     7/1986  Naples et al.
(Continued)

FOREIGN PATENT DOCUMENTS

AU    2012201634 A1    4/2012
EP     0580928 A1     2/1994
(Continued)

OTHER PUBLICATIONS

International Search Report and Written Opinion for PCT/US2014/035957 mailed Nov. 11, 2014.
(Continued)

*Primary Examiner* — Allen Porter, Jr.
(74) *Attorney, Agent, or Firm* — Lowe Graham Jones PLLC; Bruce E. Black

(57) ABSTRACT

An implantable electrical stimulation lead includes a lead body, electrodes disposed along a distal end of the lead body, terminals disposed along the proximal end of the lead body, and conductors coupling the terminals to the electrodes. The electrodes include a tip electrode having an electrode body with an outer stimulating surface. An internal lumen is defined in the electrode body and extends inwardly from an opening in a proximal end of the electrode body. Side apertures are formed between the outer stimulating surface and the internal lumen. A portion of the lead body is disposed within the internal lumen and side apertures through the opening in the proximal end of the electrode body. That portion of the lead body facilitates retention of the tip electrode on a distal tip of the lead body.

7 Claims, 12 Drawing Sheets

(51) Int. Cl.
  *A61N 1/36*     (2006.01)
  *B29C 70/84*    (2006.01)
  *B29C 45/14*    (2006.01)

(52) U.S. Cl.
  CPC ............... *A61N 1/3605* (2013.01); *A61N 1/36* (2013.01); *B29C 70/84* (2013.01); *B29C 2045/14122* (2013.01); *Y10T 29/49117* (2015.01); *Y10T 29/49172* (2015.01); *Y10T 29/49208* (2015.01)

(56) References Cited

U.S. PATENT DOCUMENTS

| | | | |
|---|---|---|---|
| 4,630,611 | A | 12/1986 | King |
| 4,744,370 | A | 5/1988 | Harris |
| 4,844,099 | A | 7/1989 | Skalsky et al. |
| 5,000,194 | A | 3/1991 | van den Honert et al. |
| 5,097,843 | A | 3/1992 | Soukup et al. |
| 5,135,001 | A | 8/1992 | Sinofsky et al. |
| 5,374,285 | A | 12/1994 | Vaiani et al. |
| 5,458,629 | A | 10/1995 | Baudino et al. |
| 5,522,874 | A | 6/1996 | Gates |
| 5,711,316 | A | 1/1998 | Elsberry et al. |
| 5,713,922 | A | 2/1998 | King |
| 5,800,350 | A | 9/1998 | Coppleson et al. |
| 5,843,148 | A | 12/1998 | Gijsbers et al. |
| 5,938,688 | A | 8/1999 | Schiff |
| 5,987,361 | A | 11/1999 | Mortimer |
| 6,018,684 | A | 1/2000 | Bartig et al. |
| 6,064,905 | A | 5/2000 | Webster, Jr. et al. |
| 6,134,478 | A | 10/2000 | Spehr |
| 6,161,047 | A | 12/2000 | King et al. |
| 6,167,311 | A | 12/2000 | Rezai |
| 6,181,969 | B1 | 1/2001 | Gord |
| 6,322,559 | B1 | 11/2001 | Daulton et al. |
| 6,510,347 | B2 | 1/2003 | Borkan |
| 6,516,227 | B1 | 2/2003 | Meadows et al. |
| 6,556,873 | B1 | 4/2003 | Smits |
| 6,564,078 | B1 | 5/2003 | Marino et al. |
| 6,609,029 | B1 | 8/2003 | Mann et al. |
| 6,609,032 | B1 | 8/2003 | Woods et al. |
| 6,678,564 | B2 | 1/2004 | Ketterl et al. |
| 6,741,892 | B1 | 5/2004 | Meadows et al. |
| 6,757,970 | B1 | 7/2004 | Kuzma et al. |
| 7,027,852 | B2 | 4/2006 | Helland |
| 7,047,084 | B2 | 5/2006 | Erickson et al. |
| 7,244,150 | B1 | 7/2007 | Brase et al. |
| 7,292,890 | B2 | 11/2007 | Whitehurst et al. |
| 7,437,193 | B2 | 10/2008 | Parramon et al. |
| 7,489,971 | B1 | 2/2009 | Franz |
| 7,668,601 | B2 | 2/2010 | Hegland et al. |
| 7,672,734 | B2 | 3/2010 | Anderson et al. |
| 7,761,165 | B1 | 7/2010 | He et al. |
| 7,761,985 | B2 | 7/2010 | Hegland et al. |
| 7,809,446 | B2 | 10/2010 | Meadows |
| 7,840,188 | B2 | 11/2010 | Kurokawa |
| 7,848,802 | B2 | 12/2010 | Goetz |
| 7,856,707 | B2 | 12/2010 | Cole |
| 7,860,570 | B2 | 12/2010 | Whitehurst et al. |
| 7,949,395 | B2 | 5/2011 | Kuzma |
| 7,974,705 | B2 | 7/2011 | Zdeblick et al. |
| 7,974,706 | B2 | 7/2011 | Moffitt et al. |
| 7,979,140 | B2 | 7/2011 | Schulman |
| 8,000,808 | B2 | 8/2011 | Hegland et al. |
| 8,019,440 | B2 | 9/2011 | Kokones et al. |
| 8,036,755 | B2 | 10/2011 | Franz |
| 8,041,309 | B2 | 10/2011 | Kurokawa |
| 8,099,177 | B2 | 1/2012 | Dahlberg |
| 8,175,710 | B2 | 5/2012 | He |
| 8,224,450 | B2 | 7/2012 | Brase |
| 8,225,504 | B2 | 7/2012 | Dye et al. |
| 8,295,944 | B2 | 10/2012 | Howard et al. |
| 8,321,025 | B2 | 11/2012 | Bedenbaugh |
| 8,364,278 | B2 | 1/2013 | Pianca et al. |
| 8,391,985 | B2 | 3/2013 | McDonald |
| 8,583,237 | B2 | 11/2013 | Bedenbaugh |
| 8,688,235 | B1 | 4/2014 | Pianca et al. |
| 2002/0147488 | A1 | 10/2002 | Doan et al. |
| 2002/0156513 | A1 | 10/2002 | Borkan |
| 2002/0183817 | A1 | 12/2002 | Van Venrooij et al. |
| 2005/0015130 | A1 | 1/2005 | Gill |
| 2005/0038489 | A1 | 2/2005 | Grill |
| 2005/0171587 | A1 | 8/2005 | Daglow et al. |
| 2006/0025841 | A1 | 2/2006 | McIntyre |
| 2006/0247697 | A1 | 11/2006 | Sharma et al. |
| 2007/0150036 | A1 | 6/2007 | Anderson |
| 2007/0203546 | A1 | 8/2007 | Stone et al. |
| 2008/0103580 | A1 | 5/2008 | Gerber |
| 2008/0114230 | A1 | 5/2008 | Addis |
| 2008/0215125 | A1 | 9/2008 | Farah et al. |
| 2009/0187222 | A1 | 7/2009 | Barker |
| 2009/0204192 | A1 | 8/2009 | Carlton et al. |
| 2009/0276021 | A1 | 11/2009 | Meadows et al. |
| 2009/0319014 | A1 | 12/2009 | Muecke et al. |
| 2010/0036468 | A1 | 2/2010 | Decre et al. |
| 2010/0076535 | A1 | 3/2010 | Pianca et al. |
| 2010/0082076 | A1 | 4/2010 | Lee et al. |
| 2010/0094387 | A1 | 4/2010 | Pianca et al. |
| 2010/0211144 | A1 | 8/2010 | Jang et al. |
| 2010/0268298 | A1 | 10/2010 | Moffitt et al. |
| 2010/0269338 | A1 | 10/2010 | Dye |
| 2010/0269339 | A1 | 10/2010 | Dye et al. |
| 2010/0287770 | A1 | 11/2010 | Dadd et al. |
| 2011/0005069 | A1 | 1/2011 | Pianca |
| 2011/0047795 | A1 | 3/2011 | Turner et al. |
| 2011/0056076 | A1 | 3/2011 | Hegland et al. |
| 2011/0077699 | A1 | 3/2011 | Swanson et al. |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0131808 | A1 | 6/2011 | Gill |
| 2011/0238129 | A1 | 9/2011 | Moffitt et al. |
| 2011/0245903 | A1 | 10/2011 | Schulte et al. |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0071949 | A1 | 3/2012 | Pianca et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | DiGiore et al. |
| 2012/0203321 | A1 | 8/2012 | Moffitt et al. |
| 2013/0197424 | A1 | 8/2013 | Bedenbaugh |
| 2013/0197602 | A1 | 8/2013 | Pianca et al. |
| 2013/0261684 | A1 | 10/2013 | Howard |
| 2013/0317587 | A1 | 11/2013 | Barker |
| 2013/0325091 | A1 | 12/2013 | Pianca et al. |
| 2014/0039587 | A1 | 2/2014 | Romero |
| 2014/0039590 | A1 | 2/2014 | Moffitt et al. |

FOREIGN PATENT DOCUMENTS

| | | |
|---|---|---|
| EP | 0650694 B1 | 7/1998 |
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 03084398 A1 | 10/2003 |
| WO | 2004045707 A1 | 6/2004 |
| WO | 2005120203 A2 | 12/2005 |
| WO | 2006029257 A2 | 3/2006 |
| WO | 2007041604 A2 | 4/2007 |
| WO | 2008018067 A2 | 2/2008 |
| WO | 2008053789 A1 | 5/2008 |
| WO | 2009025816 A1 | 2/2009 |
| WO | 2009102536 A1 | 8/2009 |
| WO | 2010083308 A1 | 7/2010 |

(56) References Cited

FOREIGN PATENT DOCUMENTS

| WO | 2013020365 A1 | 3/2013 |
|---|---|---|
| WO | 2013162775 A2 | 10/2013 |
| WO | 2014018092 A1 | 1/2014 |

OTHER PUBLICATIONS

Official Communication for U.S. Appl. No. 13/899,350 mailed Jan. 16, 2014.
International Search Report and Written Opinion mailed Sep. 26, 2013 for PCT/US2013/042014.
International Search Report and Written Opinion for PCT Application No. PCT/US2014/035957 mailed Jul. 29, 2014.
U.S. Appl. No. 14/286,940, filed May 23, 2014.
U.S. Appl. No. 14/286,889, filed May 23, 2014.
U.S. Appl. No. 14/286,934, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,829, filed May 23, 2014.
U.S. Appl. No. 14/469,214, filed Aug. 26, 2014.
U.S. Appl. No. 14/286,797, filed May 23, 2014.

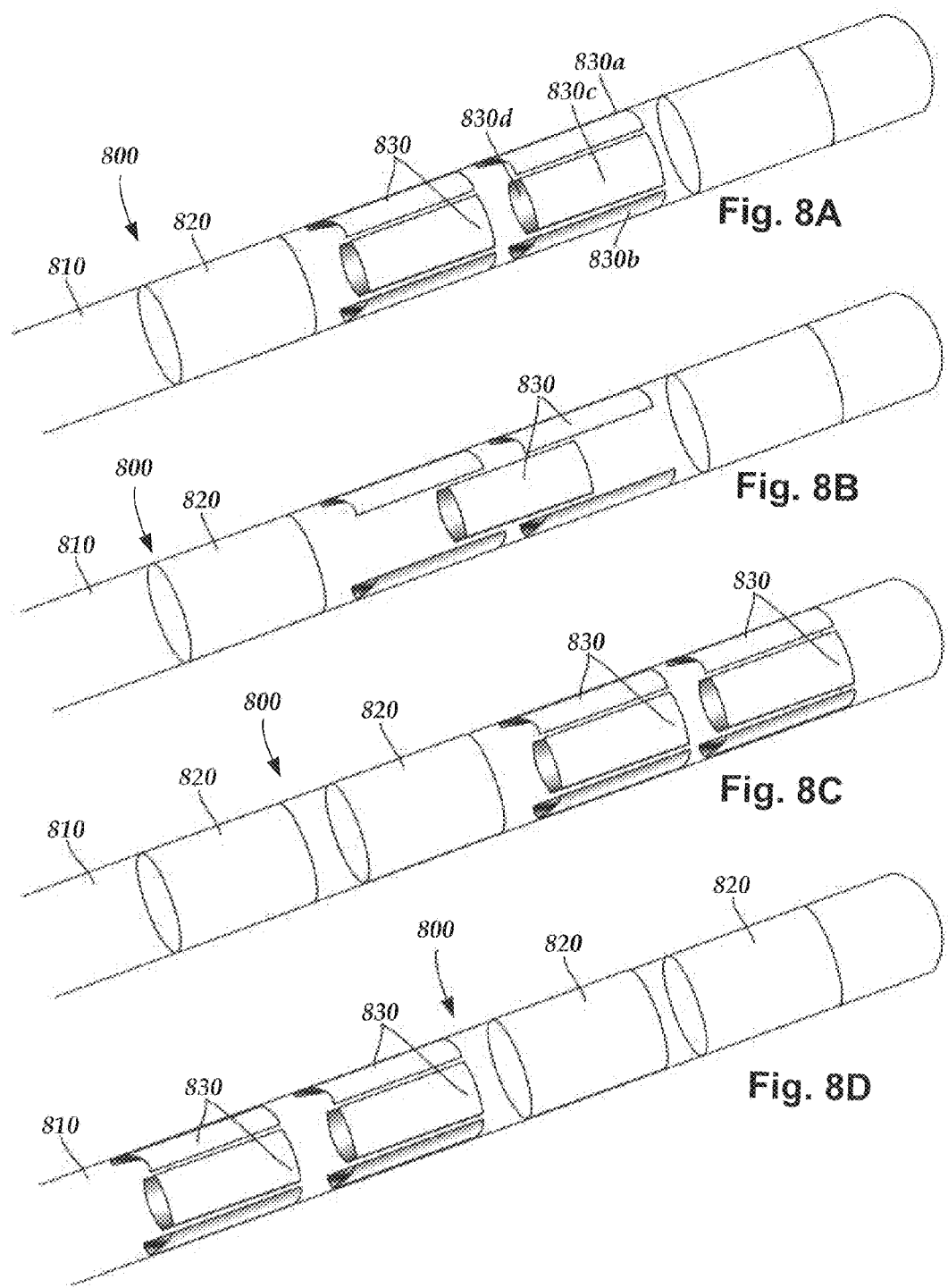

SYSTEMS AND METHODS FOR MAKING AND USING TIP ELECTRODES FOR LEADS OF ELECTRICAL STIMULATION SYSTEMS

CROSS-REFERENCE TO RELATED APPLICATIONS

This application claims the benefit under 35 U.S.C. §119(e) of U.S. Provisional Patent Application Ser. No. 61/823,743 filed May 15, 2013, which is incorporated herein by reference.

FIELD

The present invention is directed to the area of implantable electrical stimulation systems and methods of making and using the systems. The present invention is also directed implantable electrical stimulation systems with leads having tip electrodes, as well as methods of making and using tire leads, tip electrodes, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments, A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, an implantable electrical stimulation lead includes a lead body having a proximal end portion, a distal end portion, a distal tip, and a longitudinal length. A plurality of electrodes is disposed along the distal end portion of the lead body. The plurality of electrodes includes a tip electrode disposed on the distal tip of the lead body. The tip electrode includes an electrode body having an outer stimulating surface, a proximal end, a closed distal end, a circumference, and a longitudinal length. An internal lumen is defined in the electrode body and extends inwardly from an opening in the proximal end of the electrode body. A plurality of side apertures is formed through the outer stimulating surface and opens into the internal lumen. A portion of the lead body is disposed within the internal lumen and the side apertures through the opening in the proximal end of the electrode body. The portion of the lead body within the internal lumen and the side apertures facilitates retention of the tip electrode on the distal tip of the lead body. A plurality of terminals is disposed along the proximal end portion of the lead body. A plurality of conductors electrically couples each of the plurality of terminals to at least one of the plurality of electrodes.

In another embodiment an implantable electrical stimulation lead includes a lead body having a proximal end portion, a distal end portion, a distal tip, and a longitudinal length. A plurality of electrodes is disposed along the distal end portion of the lead body. The plurality of electrodes includes a tip electrode disposed on the distal tip of the lead body. The tip electrode includes an electrode body having an outer stimulating surface, a proximal end, a closed distal end, a circumference, and a longitudinal length. An internal lumen is defined in the electrode body and extends inwardly from an opening in the proximal end of the electrode body. The internal lumen defines a plurality of longitudinal grooves that extend deeper into the electrode body than adjacent portions of the internal lumen. Each of the plurality of longitudinal grooves extends along the inner surface in a direction that is parallel to the longitudinal length of the electrode body. A portion of the lead body is disposed within the internal lumen and the longitudinal grooves through the opening in the proximal end of the electrode body. The portion of the lead body within the internal lumen and the longitudinal grooves facilitates retention of the tip electrode on the distal tip of the lead body and hinders rotation of the tip electrode around the distal tip of the lead body. A plurality of terminals is disposed along the proximal end portion of the lead body. A plurality of conductors electrically couples each of the plurality of terminals to at least one of the plurality of electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 8A is a perspective view of an embodiment of a portion of a lead having a plurality of segmented electrodes, according to the invention;

FIG. 8B is a perspective view of a second embodiment of a portion of a bad having a plurality of segmented electrodes, according to the invention;

FIG. 8C is a perspective view of a third embodiment of a portion of a lead having a plurality of segmented electrodes, according to the invention;

FIG. 8D is a perspective view of a fourth embodiment of a portion of a lead having a plurality of segmented electrodes, according to the invention.

DETAILED DESCRIPTION

The present invention is directed to the area of implantable electrical stimulation systems and methods of making and using the systems. The present invention is also directed implantable electrical stimulation systems with leads having tip electrodes, as well as methods of making and using the leads, tip electrodes, and electrical stimulation systems.

Suitable implantable electrical stimulation systems include, but are not limited to, at least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
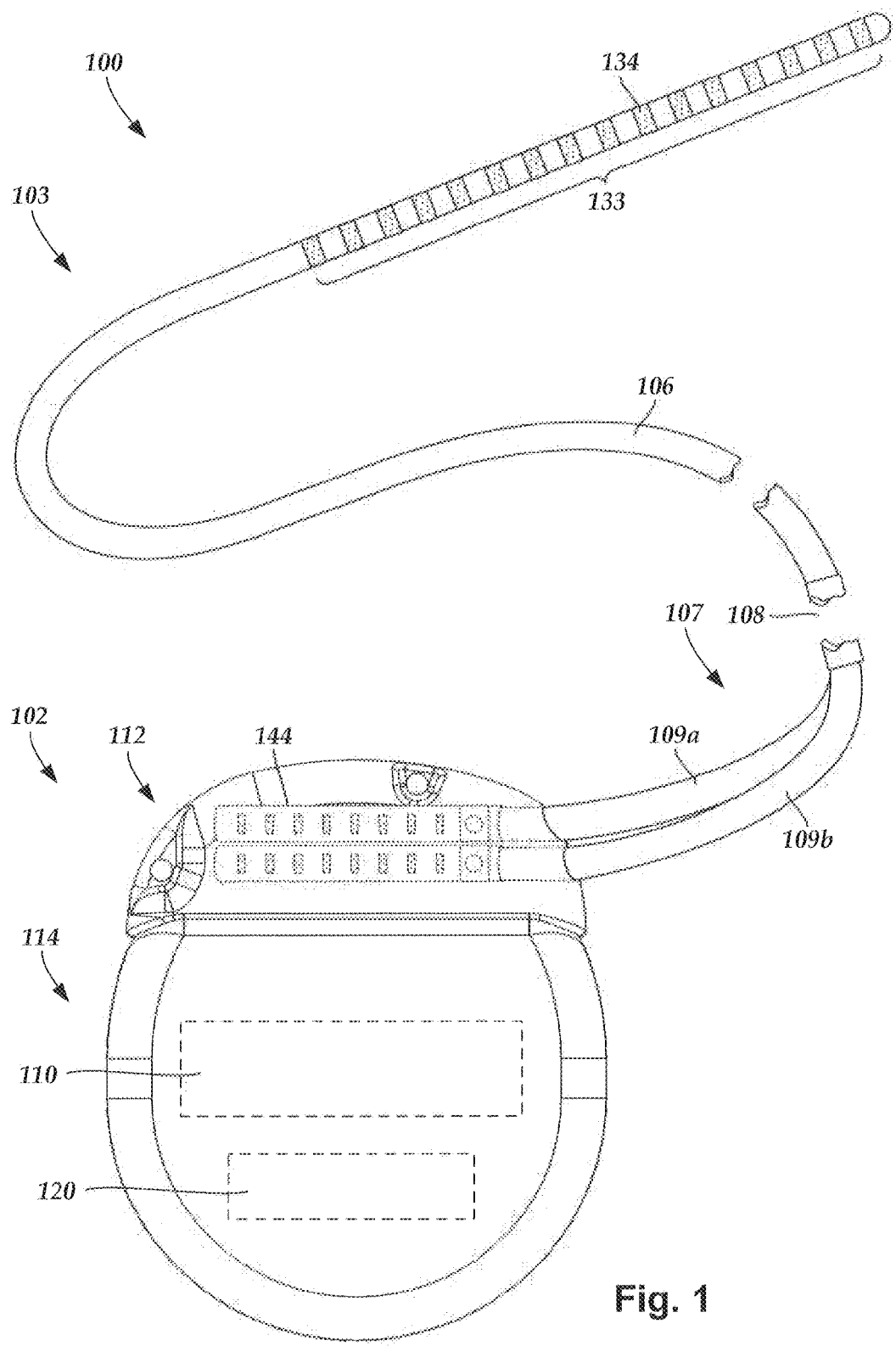
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof it will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
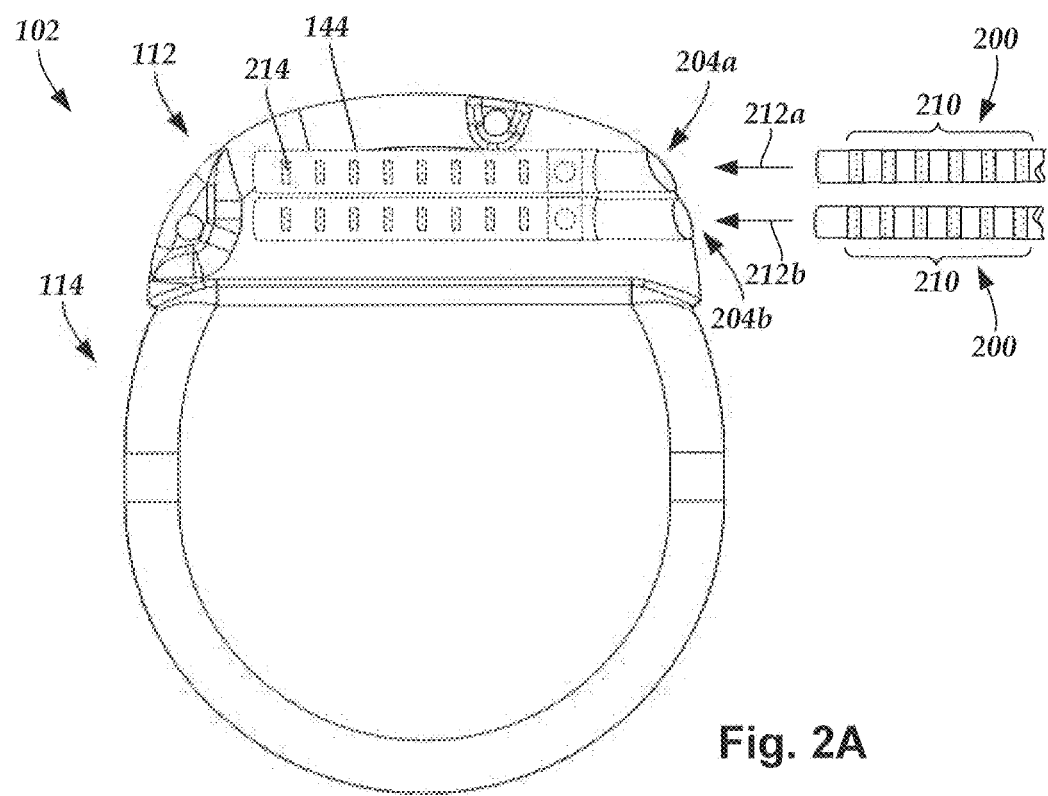
FIG. 2A is a schematic view of one embodiment of the control module of FIG. 1 configured and arranged to electrically couple to an elongated device, according to the invention.
Figure 2B:
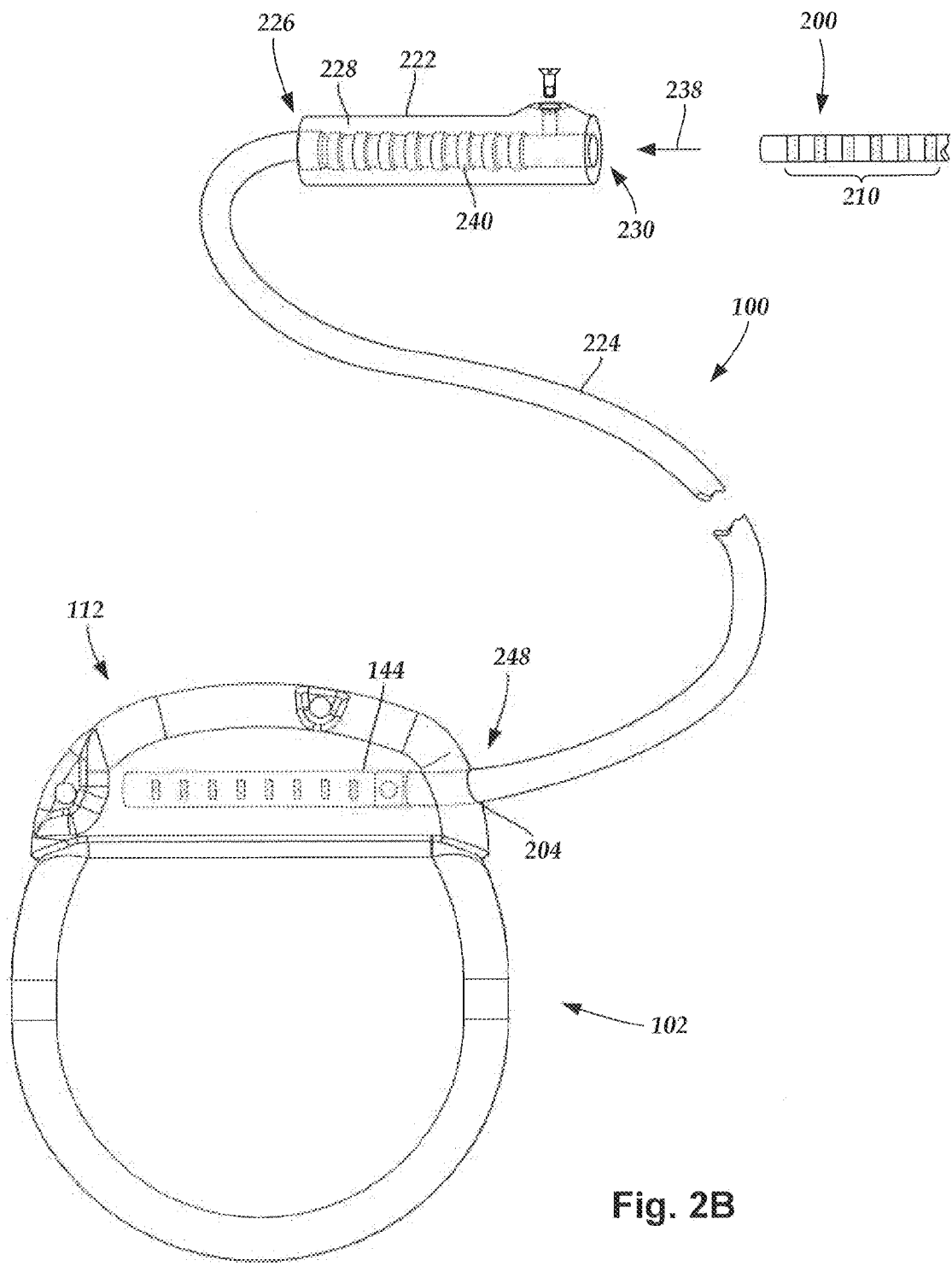
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2A-2B; and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal, in at least some embodiments, each terminal is only connected to one electrode 134.

The electrically conductive wires ("conductors") may be embedded in the non-conductive material of the lead body 106 or can be disposed in one or more lumens (not shown) extending along the lead body 106, in some embodiments, there is an individual lumen for each conductor. In other embodiments, two or more conductors extend through a lumen. There may also be one or more lumens (not shown) that open at, or near, the proximal end of tire lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably scalable at the distal end.

FIG. 2A is a schematic side view of one embodiment of a proximal end of one or more elongated devices 200 configured and arranged for coupling to one embodiment of the control module connector 144. The one or more elongated devices may include, tor example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, bar example, one, two, three, tour, live, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103.

Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144, Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Figure 7:
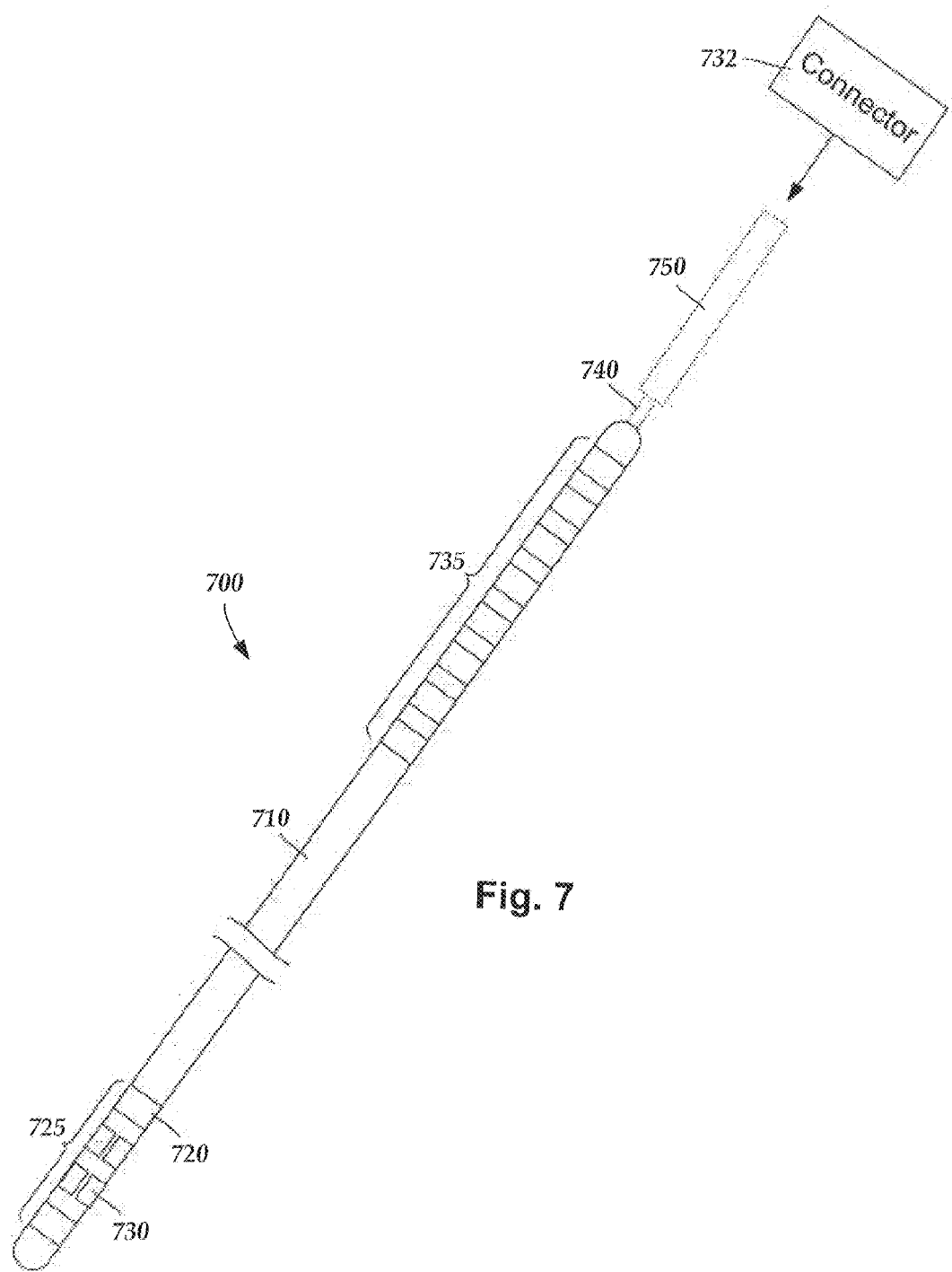
FIG. 7 is a schematic side view of one embodiment of a device for brain stimulation, according to the invention.
Figure 8E:
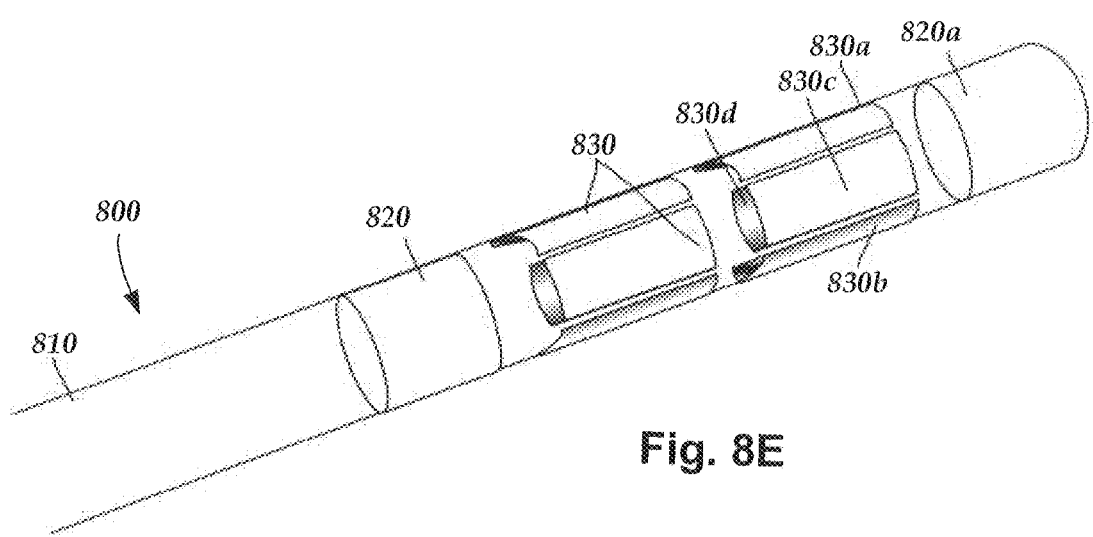
FIG. 8E is a perspective view of a fifth embodiment of a portion of a lead having a plurality of segmented electrodes, according to the invention.

Turning to FIGS. 7-8E, in some embodiments leads (e.g., percutaneous leads) are used in electrical stimulation systems designed tor brain stimulation. FIG. 7 illustrates one embodiment of a device 700 for brain stimulation. The device includes a lead 710, a plurality of electrodes 725 disposed at least partially about a circumference of the lead 710, a plurality of terminals 735, a connector 732 for connection of the electrodes to a control unit, and a stylet 740 for assisting in insertion and positioning of the lead in the patient's brain. The stylet 740 can be made of a rigid material. Examples of suitable materials for the stylet include, but are not limited to, tungsten, stainless steel, and plastic. The stylet 740 may have a handle 750 to assist insertion into the lead 710, as well as rotation of the stylet 740 and lead 710. The connector 732 fits over a proximal end of the lead 710, preferably after removal of the stylet 740.

The control unit (not shown) is typically an implantable pulse generator that can be implanted into a patient's body, for example, below the patient's clavicle area. The pulse generator can have, for example, eight stimulation channels which may be independently programmable to control the magnitude of the current stimulus from each channel. In some cases the pulse generator can have more or fewer than eight stimulation channels (e.g., 4-, 6-, 16-, 32-, or more stimulation channels). The control unit can have one, two, three, four, or more connector ports, for receiving the plurality of terminals 735 at the proximal end of the lead 710.

In one example of operation, access to the desired position in the brain can be accomplished by drilling a hole in the patient's skull or cranium with a cranial drill (commonly referred to as a burr), and coagulating and incising the dura mater, or brain covering. The lead 710 can be inserted into the cranium and brain tissue with the assistance of the stylet 740. The lead 710 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 710, retract the lead 710, or rotate the lead 710.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 710 for deep brain stimulation can include stimulation electrodes, recording electrodes, or both. In at least some embodiments, the lead 710 is rotatable so that the stimulation electrodes can be aligned with the target neurons alter the neurons have been located using the recording electrodes.

Stimulation electrodes may be disposed on the circumference of the lead 710 to stimulate the target neurons, Stimulation electrodes may be ring-shaped so that current projects from each electrode equally in every direction from the position of the electrode along a length of the lead 710. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that ail configurations of the stimulation electrodes discussed may be utilized in arranging recording electrodes as well.

The lead 700 includes a lead body 710, one or more optional ring electrodes 720, and a plurality of sets of segmented electrodes 730. The lead body 710 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 700 may be in contact with body tissue for extended periods of time. In at least some embodiments, the lead 700 has a cross-sectional diameter of no more man 1.5 mm and may be in the range of 0.5 to 1.5 mm, in at least some embodiments, the lead 700 has a length of at least 10 cm and the length of the lead 700 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 720 can be disposed on any part of the lead body 710, usually along a distal end portion of the lead 700. In FIG. 7, the lead 700 includes two ring electrodes 720. Any number of ring electrodes 720 can be disposed along the length, of the lead body 710 including, for example, one, two three, four, five, six, seven, eight, nine, ten, eleven, twelve, thirteen, fourteen, fifteen sixteen or more ring electrodes 720. It will be understood that any number of ring electrodes can be disposed along the length of the lead body 710. In some embodiments, the ring electrodes 720 are substantially cylindrical and wrap around the entire circumference of the lead body 710. In some embodiments, the outer diameters of the ring electrodes 720 are substantially equal to the outer diameter of the lead body 710. The length of the ring electrodes 720 may vary according to the desired treatment and the location of the target neurons. In some embodiments the length of the ring electrodes 720 are less than or equal to the diameters of the ring electrodes 720. In other embodiments, the lengths of the ring electrodes 720 are greater than the diameters of the ring electrodes 720, As discussed in more detail below, the distal-most ring electrode 720 may be a tip electrode (see e.g., tip electrode 820a of FIG. 8E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may he located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803: 2011/0130816; 2011/0130817; 2011/0130818; 2011/0078900; 2011/0238129; 2012/0016378; 2012/0046710; 2012/0071949: 2012/0165911: 2012/197375; 2012/0203316; 2012/0203320; 2012/0203321, all of which are incorporated herein by reference.

The lead 700 is shown having a plurality of segmented electrodes 730. Any number of segmented electrodes 730 may be disposed on the lead body 710 including, for example, one, two three, four, five, six, seven, eight, nine, ten, eleven, twelve, thirteen, fourteen, fifteen, sixteen or more segmented electrodes 730. It will he understood that any number of segmented electrodes 730 may be disposed along the length of the lead body 710. A segmented electrode 730 typically extends only 75%, 67%, 60%, 50%, 40%, 33%, 25%, 20%, 17%, 15%, or less around the circumference of the lead.

The segmented electrodes 730 may be grouped into sets of segmented electrodes, where each set is disposed around a circumference of the lead 700 at a particular longitudinal portion of the lead 700. The lead 700 may have any number segmented electrodes 730 in a given set of segmented electrodes. The lead 700 may have one, two, three, four, five, six, seven, eight, or more segmented electrodes 730 in a given set. In at least some embodiments, each set of segmented electrodes 730 of the lead 700 contains the same number of segmented electrodes 730. The segmented electrodes 730 disposed on the lead 700 may include a different number of electrodes than at least one other set of segmented electrodes 730 disposed on the lead 700.

The segmented electrodes 730 may vary m size and shape. In some embodiments, the segmented electrodes 730 are all of the same size, shape, diameter, width or area, or any combination thereof in some embodiments, the segmented electrodes 730 of each circumferential set (or even all segmented electrodes disposed on the lead 700) may be identical in size and shape.

Each set of segmented electrodes 730 may be disposed around the circumference of the lead body 710 to form a substantially cylindrical shape around the lead body 710. The spacing between individual electrodes of a given set of the segmented electrodes may be the same, or different from, the spacing between individual electrodes of another set of segmented electrodes on the lead 700. In at least some embodiments, equal spaces, gaps or cutouts are disposed between each segmented electrode 730 around the circumference of the lead body 710. In other embodiments, the spaces, gaps or cutouts between the segmented electrodes 730 may differ in size or shape. In other embodiments, the spaces, gaps, or cutouts between segmented electrodes 730 may be uniform for a particular set of the segmented electrodes 730, or for all sets of the segmented electrodes 730, The sets of segmented electrodes 730 may be positioned in irregular or regular intervals along a length the lead body 710.

Conductor wires that attach to the ring electrodes 720 or segmented electrodes 730 extend along the lead body 710. These conductor wires may extend through the material of the lead 700 or along one or more lumens defined by the lead 700, or both. The conductor wires are presented at a connector (via terminals) for coupling of the electrodes 720, 730 to a control unit (not shown).

When the lead 700 includes both ring electrodes 720 and segmented electrodes 730, the ring electrodes 720 and the segmented electrodes 730 may be arranged in any suitable configuration. For example, when the lead 700 includes two sets of ring electrodes 720 and two sets of segmented electrodes 730, the ring electrodes 720 can flank the two sets of segmented electrodes 730 (see e.g., FIG. 7). Alternately, the two sets of ring electrodes 720 can be disposed proximal to the two sets of segmented electrodes 730 (see e.g., FIG. 8C), or the two sets of ring electrodes 720 can be disposed distal to the two sets of segmented electrodes 730 (see e.g., FIG. 8D). One of the ring electrodes can be a tip electrode (see, tip electrode 820a of FIG. 8E). It will be understood that other configurations are possible as well (e.g., alternating ring and segmented electrodes, or the like).

By varying the location of the segmented electrodes 730, different coverage of the target neurons may be selected. For example, the electrode arrangement of FIG. 8C may be useful if the physician anticipates that the neural target will be closer to a distal tip of the lead body 710, while the electrode arrangement of FIG. 8D may be useful if the physician anticipates that the neural target will, be closer to a proximal end of the lead body 710.

Any combination of ring electrodes 720 and segmented electrodes 730 may be disposed on the lead 700. For example, the lead may include a first ring electrode 720, two sets of segmented electrodes; each set formed of four segmented electrodes 730, and a final ring electrode 720 at the end of the lead. This configuration may simply be referred to as a 1-4-4-1 configuration (FIGS. 8A and 8E). It may be useful to refer to the electrodes with this shorthand notation. Thus, the embodiment of FIG. 8C may be referred to as a 1-1-4-4 configuration, while the embodiment of FIG. 8D may be referred to as a 4-4-1-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 730 are disposed, on the lead. Another electrode configuration is a 1-3-3-1 configuration with two sets of segmented electrodes, each set containing three electrodes disposed around the circumference of the lead, flanked by two ring electrodes or a ring electrode and a tip electrode. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

In some embodiments, measurement devices coupled to the muscles or other tissues stimulated by the target neurons or a unit, responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example. If the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

When the lead 700 includes a plurality of sets of segmented electrodes 730, it may be desirable to form the lead 700 such that corresponding electrodes of different sets of segmented electrodes 730 are longitudinally aligned with one another along the length of the lead 700 (see e.g., the segmented electrodes 730 shown in FIG. 7). Longitudinal alignment between corresponding electrodes of different sets of segmented electrodes 730 along the length of the lead 700 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the bad 700 are longitudinally aligned with one another and do not circumferentially shift in relation to one another during manufacturing of the lead 700.

In other embodiments, individual electrodes in the two sets of segmented electrodes 730 are staggered (see, FIG. 8B) relative to one another along the length of the lead body 711). In some cases, the staggered positioning of corresponding electrodes of different sets of segmented electrodes along the length of the lead 700 may be designed for a specific application.

FIGS. 8A-8E illustrate leads 800 with segmented electrodes 830, optional ring electrodes 820 or tip electrodes 820a, and a lead body 810. The sets of segmented electrodes 830 include either two (FIG. 8B) or four (FIGS. 8A, 8C, and 8D) or any other number of segmented electrodes including, for example, three, five, six, or more.

Any other suitable arrangements of segmented electrodes can be used. As an example, arrangements in which segmented electrodes are arranged helically with respect to each other. One embodiment includes a double helix.

As mentioned above (FIG. 8E), a tip electrode can be used in combination with one or more circumferential electrodes (e.g., one or more ring electrodes, one or more segmented electrodes, or any combination of one or more ring electrodes and one or more segmented electrodes). In at least some embodiments, a tip electrode may be selected to have the same, or substantially the same, surface area as one or more ring electrodes of the lead.

Figure 3:
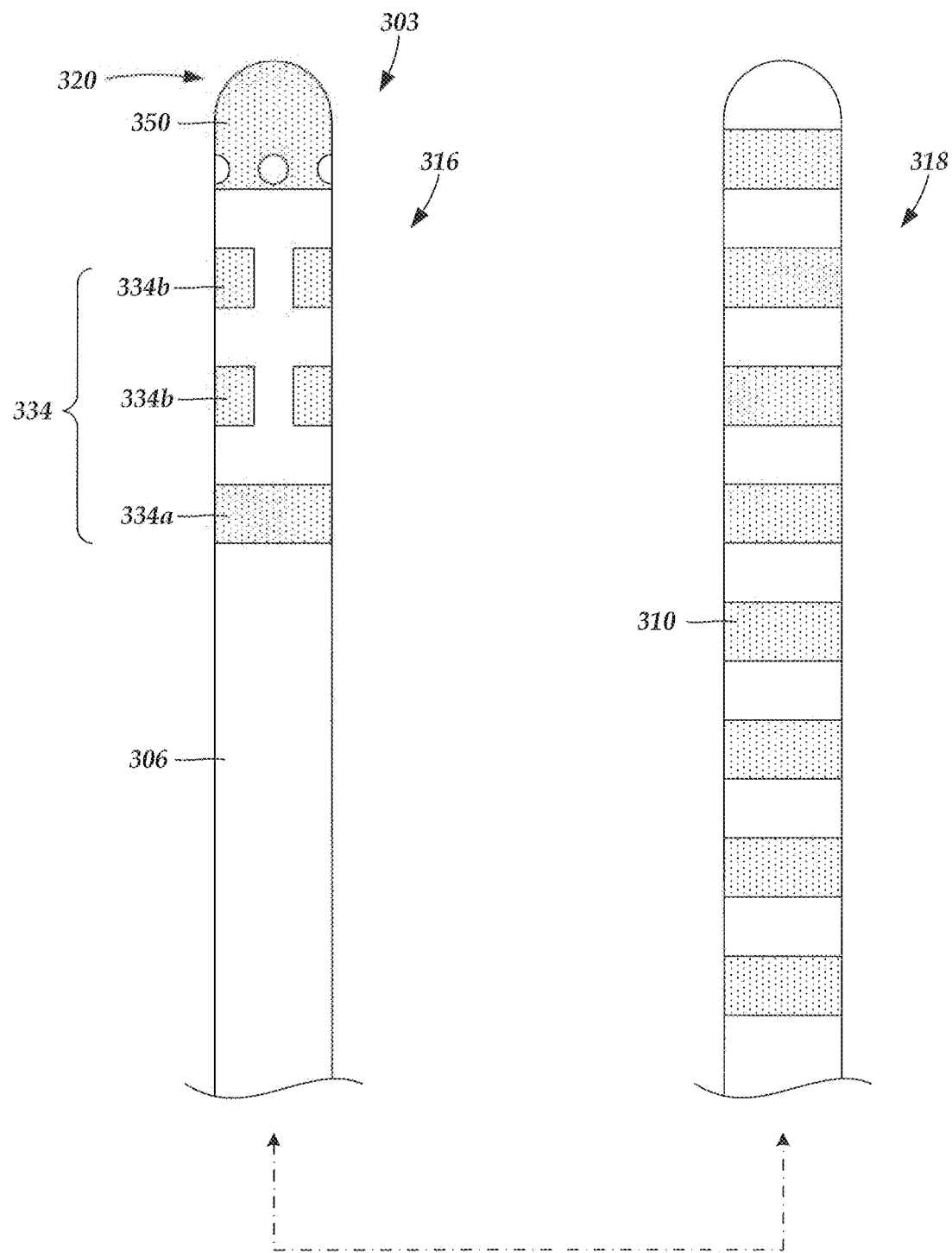
FIG. 3 is a schematic side view of one embodiment of a distal end portion and a proximal end portion of a lead body, the lead body having a tip electrode and circumferential electrodes disposed along the distal end portion and terminals disposed along the proximal end portion, according to the invention.

Turning to FIG. 3, a tip electrode can be designed to improve retention of the tip electrode on a lead, or to prevent undesired rotation of the tip electrode relative to the lead body, or both. As herein described, a tip electrode includes one or more lead-retention features, such as one or more channels, side apertures, or longitudinal grooves, that are defined along a body of the tip electrode and that improve retention of the tip electrode on the lead, or that prevent undesired rotation of the tip electrode relative to the lead body, or both.

FIG. 3 illustrates a side view of one embodiment of a distal end portion 316 and a proximal end portion 318 of a lead body 306 of a lead 303. The distal end portion 316 of the lead body 306 includes a distal tip 320. Terminals, such as terminal 310, are disposed along the proximal end portion 318 of the lead body 306.

A tip electrode 350 is disposed along the distal tip 320 of the lead body 306. In at least some embodiments, the tip electrode 350 has a rounded distal end. In at least some embodiments, the tip electrode 350 has a closed distal end. Circumferential electrodes 334 are disposed along the distal end portion 316 of the lead body 306. In FIG. 3, the circumferential electrodes 334 include a ring electrode 334a and multiple segmented electrodes 334b.

Any suitable number of circumferential electrodes 334 can be disposed along the distal end portion 316 of the lead including, for example, one, two, three, four, five, six, seven, eight, nine, ten, eleven, twelve, fourteen, sixteen, twenty, twenty-four, or more circumferential electrodes 334. The total number of circumferential electrodes 334 can include any combination of ring electrodes and segmented electrodes, including all ring electrodes and no segmented electrodes, or all segmented electrodes and no ring electrodes.

The segmented electrodes 334b are typically grouped into sets of segmented electrodes that are disposed around a particular circumference of the lead body 306 and that are physically and electrically isolated from one another. A set of segmented electrodes 334b can include any suitable number of segmented electrodes including, for example, two, three, four, five, six, or more segmented electrodes, in at least some embodiments, a single segmented electrode is disposed around a portion of a particular circumference of the lead body that is not part of a set of segmented electrodes.

In at least some embodiments, the circumferential electrodes 334 are isodiametric with the lead body 306. In at least some embodiments, the tip electrode 350 is isodiametric with the lead body 306. In at least some embodiments, the circumferential electrodes 334 and the tip electrode 350 are each isodiametric with the lead body 306.

The circumferential electrodes 334 can be disposed along the distal end portion 316 of the lead body 306 in any suitable configuration. In at least some embodiments, the distal-moss, circumferential electrode 334 is a segmented electrode 334b. In at least some other embodiments, the distal-most circumferential electrode 334 is a ring electrode 334a.

In at least some embodiments, the lead body 306 is formed by molding the lead body 306 between the circumferential electrodes 334 and, at least in some embodiments, between the circumferential electrodes 334 and the terminals 310. The material of the lead body 306 can also be molded between the distal-most circumferential electrode 334 and the tip electrode 350.

During the molding process, the material that will form the lead body can flow into an internal lumen (470 in FIGS. 4A-4B) of the tip electrode 350. Any molding process can be used including, but not limited to, injection molding. The lead body 306 can be formed of any material that can be molded by flowing the material around fee other components and then solidity the material to form, the lead body. Any suitable process can be used, to solidify the material including, but not limited to, cooling the material, photo-curing, heat curing, cross-linking, and the like. Examples of suitable materials can include silicone, polyurethane, polyetheretherketone, epoxy, and the like. As an example, the methods for forming a lead, with segmented, electrodes disclosed in U.S. Patent Application Publication No. 2011/0078900, incorporated herein by reference, can be modified to include a tip electrode (by, for example, replacing the distal-most ring electrode in FIGS. 7A-7E with a tip electrode).

Figure 4A:
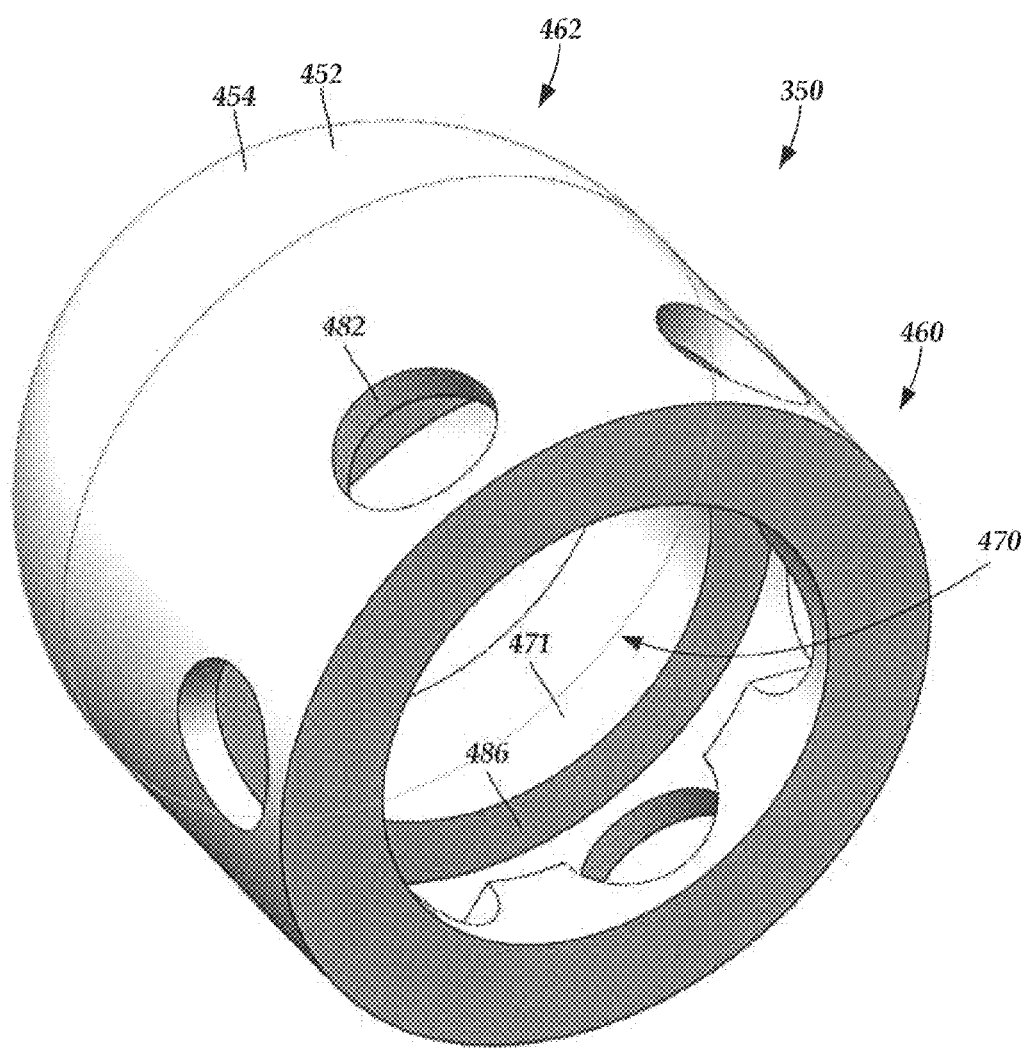
FIG. 4A is a schematic perspective view of one embodiment of the tip electrode of FIG. 3. the tip electrode including a channel and multiple side apertures defined along an internal lumen of the tip electrode, according to the invention.
Figure 4B:
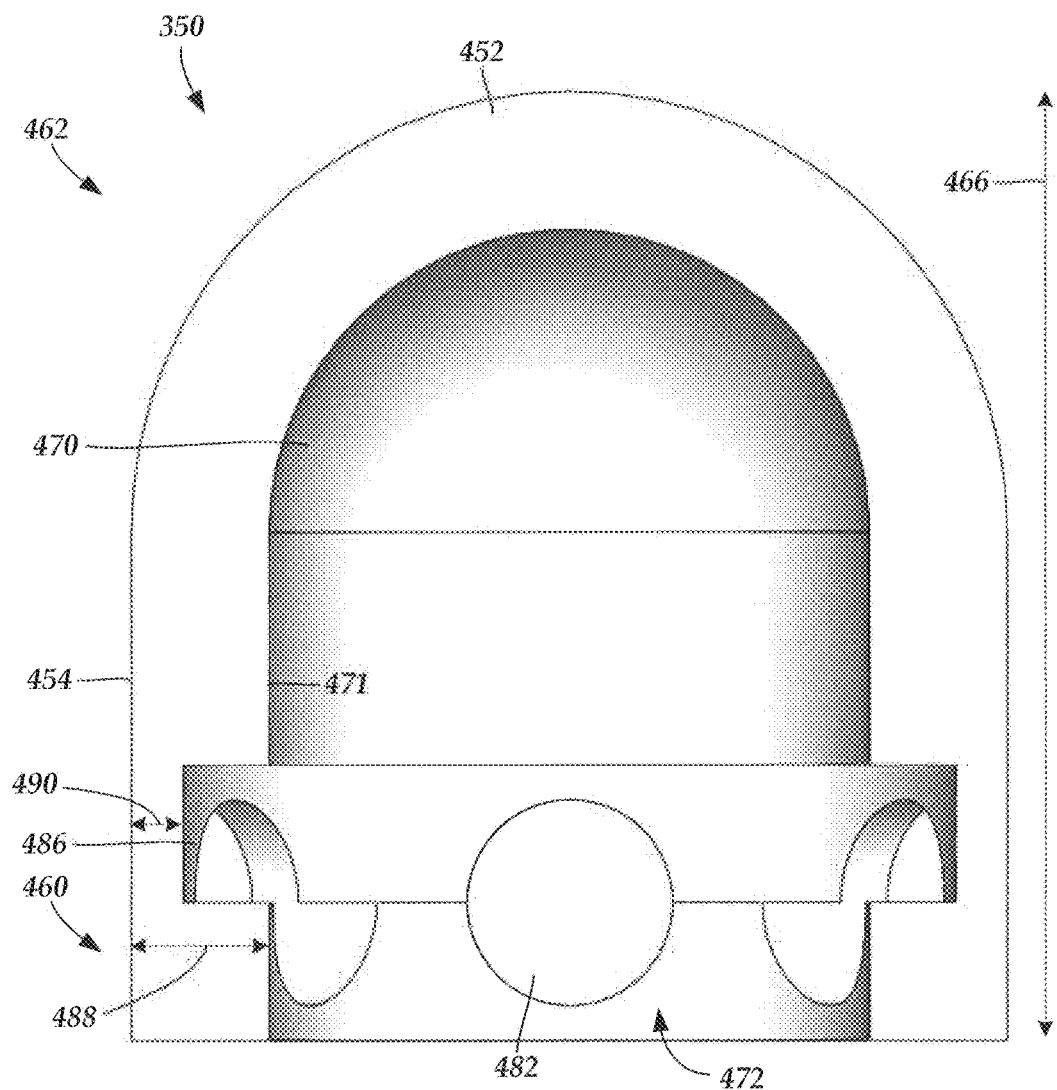
FIG. 4B is a schematic longitudinal cross-sectional view of one embodiment of the tip electrode of FIG. 4A, the tip electrode including a channel and multiple side apertures defined along an internal lumen of the tip electrode, according to the invention.

FIG. 4A illustrates a schematic perspective view of one embodiment of the tip electrode 350. FIG. 4B illustrates a schematic longitudinal cross-section of the tip electrode 350. The tip electrode 350 includes an electrode body 452 having an outer stimulating surface 454. The electrode body 452 has a proximal end 460, a distal end 462, a longitudinal length 466, and a circumference. At least a portion of the outer stimulating surface 454 of the electrode body 452 is exposed to tissue, when the lead 303 is implanted, for providing stimulation to patient tissue.

The electrode body 452 can have any suitable cross-sectional shape along an axis transverse to the longitudinal length 466. In at least some embodiments, the electrode body 452 has a round transverse cross-sectional shape. In at least some embodiments, the distal end 462 of the electrode body 452 is rounded along an axis parallel with the longitudinal length 466. In at least some embodiments, the distal end 462 of the electrode body 452 is closed.

The tip electrode 350 defines an internal lumen 470 having a lumen surface 471. The internal lumen 470 extends inwardly from an opening 472 defined in the proximal end 460 of the electrode body 452. The internal lumen 470 can extend inwardly from the opening 472 along any suitable portion of the longitudinal length 466 of the electrode body 452 including, for example, at least 75%, 80%, 85%, 90%, 92%, 94%, 96%, 98%, or more of the longitudinal length 466 of the electrode body 452. The internal lumen 470 can have any suitable shape along a plane that is transverse to the longitudinal length of the tip electrode 350. In at least some embodiments, the internal lumen 470 each has a round transverse shape.

The tip electrode defines one or more lead-retention features. In at least some embodiments, one or more of the lead-retention features are at least partially formed along internal lumen surfaces of the tip electrode. As mentioned above, when the lead body is formed, the material of the lead body flows into the internal lumen and solidities. The one or more lead-retention features form shapes that, when material of the lead body is flowed into and solidifies, are configured and arranged to facilitate retention of the tip electrode on the lead body of the resulting lead, or prevent undesired rotation of the tip electrode relative to the lead body, or both.

In at least some embodiments, the tip electrode 350 defines multiple side apertures, such as side aperture 482, defined along the surface 471 of the internal lumen 470. The side apertures 482 extend deeper into the electrode body 452 than adjacent portions of the internal lumen 470. In other words, the side apertures 482 extend radially outward from the internal lumen. The side apertures 482 are configured and arranged to facilitate retention of the tip electrode 350 on the lead body 306 and also to resist rotation of the tip electrode 350 around the lead body 306.

Any suitable number of side apertures can be defined in the internal lumen including, for example, two, three, four, five, six. seven, eight, nine, ten, eleven, twelve, or more side apertures 482. The side apertures can be defined along any suitable locations of the internal lumen. In at least some embodiments, at least one of the side apertures is defined along the proximal end of the electrode body. In FIGS. 4A-4B, each of the side apertures 482 is shown defined, along the proximal end 460 of the electrode body 452. In at least some embodiments, the side apertures are each defined along a plane transverse, or substantially transverse, to the longitudinal length of the electrode body.

In some embodiments, at least one of the side apertures extends partially through a thickness of the electrode body 452 and does not open to the outer stimulating surface 454. In at least some embodiments, at least one of the side apertures extends entirely through the thickness of the electrode body and opens to the outer stimulating surface. In other words, in at least some embodiments at least one of the side apertures is formed through the outer stimulating surface and opens into the internal lumen. In FIGS. 4A-4B, each of the side apertures 482 is shown extending entirely through the thickness of the electrode body 452 between the outer stimulating surface 454 and the internal lumen 470.

When material of the lead body flows into the internal lumen 470, some of the material flows from the internal lumen 470 into the side apertures 482. Once the material solidifies, the tip electrode 350 is prevented from rotating and from being removed from the lead body 306. In cases where one or more of the side apertures open to the outer stimulating surface 454, some material may flow out of side aperture during manufacture and onto the outer stimulating surface of the tip electrode. Any such material may subsequently be removed by grinding the outer stimulating surface 456 of the tip electrode 350.

In at least some embodiments, the tip electrode defines one or more channels 486 extending along the surface 471 of the internal lumen 470. The one or more channels 486 extend deeper into the electrode body 452 than adjacent portions of the internal lumen 470. In other words, the one or more channels 486 extend radially outward from the internal lumen. The one or more channels 486 are configured and arranged to facilitate retention of the tip electrode on the lead body. When material of the lead body flows into the internal lumen 470, some of the material flowing into the internal lumen 470 flows into the one or more channels 486. Once the material solidifies, the material resists movement of the tip electrode relative to the lead body.

Any suitable number of channels 486 can be defined in the internal lumen including, for example, one, two, three, four, five, or more channels 486. The channels 486 can be defined along any suitable locations of the internal lumen.

In at least some embodiments, the one or more channels 486 extend along at least a portion of the circumference of the electrode body 452. In at least some embodiments, at least one of the one or more channels 486 extends at least 25%, 50%, or 75% around the circumference of the tip electrode, in at least some embodiments, at least one of the one or more channels 486 extends around the entire circumference of the tip electrode. In at least some embodiments, at least one of the channels 486 is defined along the proximal end of the tip electrode. In FIGS. 4A-4B, a single channel 486 is shown extending around the entire circumference of the tip electrode along a proximal end portion of the tip electrode.

In at least some embodiments, at least one of the one or more channels 486 extends through at least a portion of the electrode body 452 along which at least one of the side apertures 482 also extends. In other words, at least one of the one or more channels 486 intersects at least one of the side apertures 482. In which case, the one or more side apertures 482 may include multiple thicknesses, for example, FIG. 4B shows the channel 486 extending along a distal portion of each of multiple side apertures 482. In FIG. 4B, the channel 486 is shown extending through only a portion of a thickness of the electrode body 452, while the side apertures 482 extend entirely through the thickness of the electrode body 452. Thus, the side apertures 482 each have a first length 488 along a proximal portion of each of the side apertures 482 and a second length 490 along a distal portion of each, of the side apertures 482, where the first length 488 is different than the second length 490.

A tip-electrode conductor (not shown) is attached, welded, soldered, or otherwise electrically coupled to the tip electrode 350. The coupling of the tip-electrode conductor may occur prior to forming the lead body 306. The tip-electrode conductor, like other conductors in the lead, extends along the lead and is electrically coupled to one of the terminals disposed along the proximal end portion of the lead. In some embodiments, the tip-electrode conductor is coupled to the tip electrode 350 along the surface 471 of the internal lumen 470.

Figure 5A:
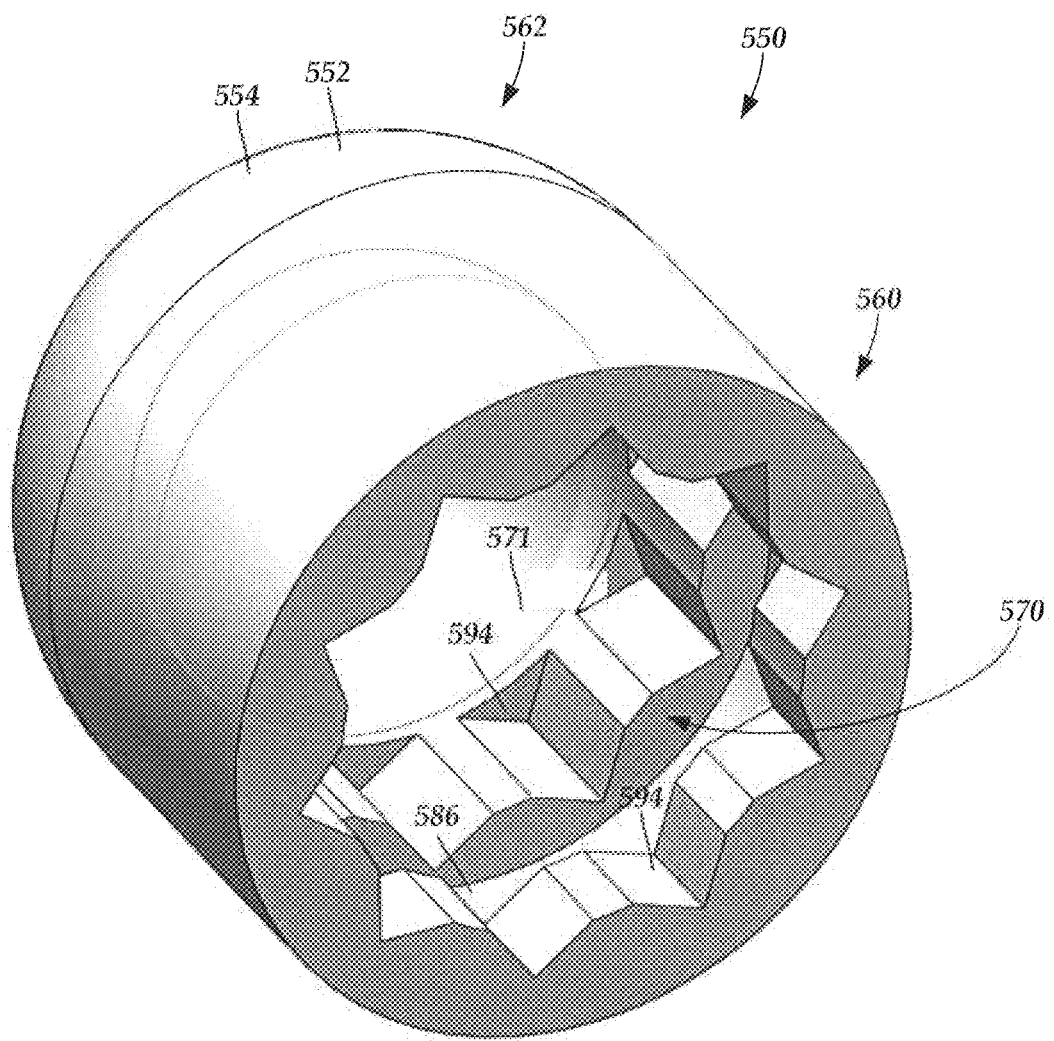
FIG. 5A is a schematic perspective view of another embodiment of a tip electrode, the tip electrode including a channel and multiple longitudinal grooves defined along an internal lumen of the tip electrode, according to the invention.
Figure 5B:
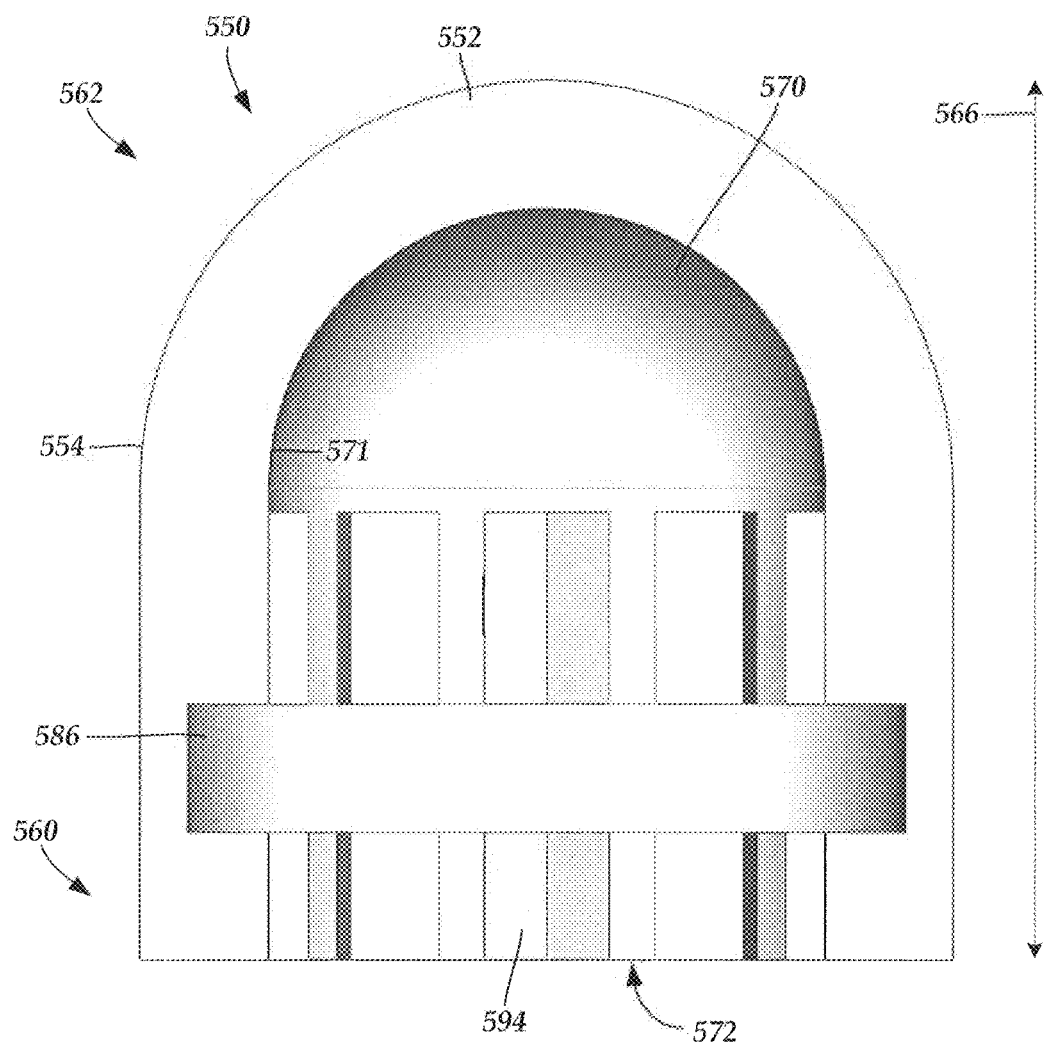
FIG. 5B is a schematic longitudinal cross-sectional view of one embodiment of the tip electrode of FIG. 5A, the tip electrode including a channel and multiple longitudinal grooves defined along an internal lumen of the tip electrode, according to the invention.

In at least some embodiments, the lead-retention features include one or more longitudinal grooves in addition to, or in lieu of the one or more side apertures shown in FIGS. 3-4B. FIG. 5A illustrates a schematic perspective view of one embodiment of a tip electrode 550. FIG. 5B illustrates a schematic longitudinal cross-section of the tip electrode 550. The tip electrode 550 is configured and arranged for attaching to the distal tip of a lead, such as the lead 303 of FIG. 3. The tip electrode 550 includes an electrode body 552 having an outer stimulating surface 554. The electrode body 552 has a proximal end 560, a distal end 562, a longitudinal length 566, and a circumference. At least a portion of the outer stimulating surface 554 of the electrode body 552 is exposed to tissue, when the lead 303 is implanted, for providing stimulation to patient tissue.

The electrode body 552 can have any suitable cross-sectional shape along an axis transverse to the longitudinal length 466. In at least some embodiments, the electrode body 552 has a round transverse cross-sectional shape. In at least some embodiments, the distal end 562 of the electrode body 552 is rounded along an axis parallel with the longitudinal length 566. In at least some embodiments, the distal end 562 of the electrode body 552 is closed.

The tip electrode 550 defines an internal lumen 570 having a lumen surface 571. The internal lumen 570 extends inwardly from an opening 572 defined in the proximal end 560 of the electrode body 552. The internal lumen 570 can extend inwardly from the opening 572 along any suitable portion of the longitudinal length 566 of the electrode body 552 including, for example, at least 75%, 80%, 85%, 90%, 92%, 94%, 96%, 98%, or more of the longitudinal length 566 of the electrode body 552. The internal lumen 570 can have any suitable shape along a plane that is transverse to the longitudinal length of the tip electrode 550. In at least some embodiments, the internal lumen 570 each has a round transverse shape.

The tip electrode defines one or more lead-retention features. As mentioned above, when the lead body is formed, the material of the lead body flows into the internal lumen and solidifies. The one or more lead-retention features form shapes that, when material of the lead body is flowed into and solidifies, are configured and arranged to facilitate retention of the tip electrode on the lead body of the resulting lead, or prevent undesired rotation of the tip electrode relative to the lead body, or both.

In at least some embodiments, the tip electrode 550 defines multiple longitudinal grooves, such as longitudinal groove 594, defined along the surface 571 of the internal lumen 570. The longitudinal grooves 594 extend deeper into the electrode body 552 than adjacent portions of the internal lumen 570. In other words, the one or more longitudinal grooves 594 extend radially outward from the internal lumen. The longitudinal grooves 594 are configured and arranged to facilitate retention of the tip electrode 550 on the lead body 306 and also to resist rotation of the tip electrode 550 around the lead body 306.

Any suitable number of longitudinal grooves can be defined along the internal lumen including, for example, two, three, four, five, six, seven, eight, nine, ten, eleven, twelve, thirteen, fourteen, fifteen, sixteen, seventeen, eighteen, nineteen, twenty, or more longitudinal grooves 594. The longitudinal grooves can be defined, along any suitable locations of the internal lumen. In at least some embodiments, at least one of the longitudinal grooves is defined along the proximal end of the electrode body. In FIGS. 5A-5B, each of the longitudinal grooves 594 is shown defined along the proximal end 560 of the electrode body 552.

The longitudinal grooves 594 can be any suitable shape. In at least some embodiments, the longitudinal grooves are elongated such that the longitudinal grooves have lengths that are at least 2, 3, 4, 5, 10, 15, 20, or more times widths of the longitudinal grooves. In at least some embodiments, the longitudinal grooves each extend parallel to one another. In at least, some embodiments, at least one of the longitudinal, grooves extends in a different direction than at least one of the other longitudinal grooves. In at least some embodiments, the longitudinal grooves each extend in a direction that is parallel, or substantially parallel, to the longitudinal length of the tip electrode.

The longitudinal grooves can be of any suitable length. In some embodiments, the longitudinal grooves extend an entire length of the internal lumen. In other embodiments, the longitudinal grooves extend less than an entire length of the internal lumen. In at least some embodiments, the longitudinal grooves extend at least 25%, 30%, 35%, 40%, 45%, 50%, 60%, or more, of the longitudinal length of the electrode body. In at least some embodiments, the longitudinal grooves extend from the opening 572 of the internal lumen.

In some embodiments, at least one of the longitudinal grooves extends partially through a thickness of the electrode body 552 and does not open to the outer stimulating surface 554. In at least some embodiments, at least one of the longitudinal grooves extends entirely through the thickness of the electrode body and opens to the outer stimulating surface. In other words, in at least some embodiments at least one of the longitudinal grooves is formed through the outer stimulating surface and opens into the internal lumen. In FIGS. 5A-5B, each of the longitudinal grooves 594 axe shown extending partially through the thickness of the electrode body 552 from the surface of the internal lumen 570 and do not open to the outer stimulating surface 554.

When material of the lead body flows into the internal lumen 570, some of the material flows from the internal lumen 570 into the longitudinal grooves 594. Once the material solidities, the tip electrode 550 is prevented from rotating and from being removed from the lead body 306. In cases where one or more of the longitudinal channels open to the outer stimulating surface 554, some material may flow out of longitudinal channels during manufacture and onto the outer stimulating surface of the tip electrode. Any such material may subsequently be removed by grinding the outer stimulating surface 556 of the tip electrode 550.

In at least some embodiments, the tip electrode defines one or more channels 586 extending along the surface 571 of the internal lumen 570. The one or more channels 586 extend deeper into the electrode body 552 than adjacent portions of the internal lumen 570. In other words, the one or more channels 586 extend radially outward from the internal lumen. The one or more channels 586 are configured and arranged to facilitate retention of the tip electrode on the lead body. When material of the lead body flows into the internal lumen 570, some of the material flowing into the internal lumen 570 flows into the one or more channels 586. Once the material solidifies, the material resists movement of the tip electrode relative to the lead body.

Any suitable number of channels 586 can be defined along the internal lumen including, for example, one, two, three, four, five, or more channels 586. The channels 586 can be defined along any suitable portions of the internal lumen. In at least some embodiments, at least one of the one or more channels 586 extends through at least a portion of the electrode body 552 along which at least one of the longitudinal grooves 594 also extends. In other words, at least one of the one or more channels 586 intersects at least one of the longitudinal grooves 594.

In at least some embodiments, the one or more channels 586 extend along at least a portion of the circumference of the electrode body 552. In at least some embodiments, at least one of the one or more channels 586 extends at least 25%, 50%, or 75% around the circumference of the tip electrode. In at least some embodiments, at least one of the one or more channels 586 extends around the entire circumference of the tip electrode. In at least some embodiments, at least one of the channels 586 is defined along the proximal end of the electrode body. In FIGS. 5A-5B, a single channel 586 is shown extending around the entire circumference of the tip electrode along the proximal end portion of the tip electrode.

In at least some embodiments, the one or more channels 586 extend more deeply into the surface 571 of the internal lumen 570 than at least one of the longitudinal grooves 594. In which case, for example, when a channel intersects a particular longitudinal groove, and when the channel extends more deeply into the surface of the internal lumen than the longitudinal groove, the channel separates that longitudinal groove into a proximal portion and a distal portion. In FIGS. 5A-5B, the single channel 586 is shown extending around the entire circumference of the electrode body 552 and extending deeper into the surface 571 of the internal lumen 570 than the longitudinal grooves 594 such that each of the longitudinal grooves 594 is separated into a proximal portion and a distal portion.

A tip-electrode conductor (not shown) is attached, welded, soldered, or otherwise electrically coupled to the tip electrode 550. The coupling of the tip-electrode conductor may occur prior to forming the lead body 306. The tip-electrode conductor, like other conductors in the lead, extends along the lead and is electrically coupled to one of the terminals disposed along the proximal end portion of the lead. In some embodiments, the tip-electrode conductor is coupled to the tip electrode 550 along the surface 571 of the internal lumen 570.

Figure 6:
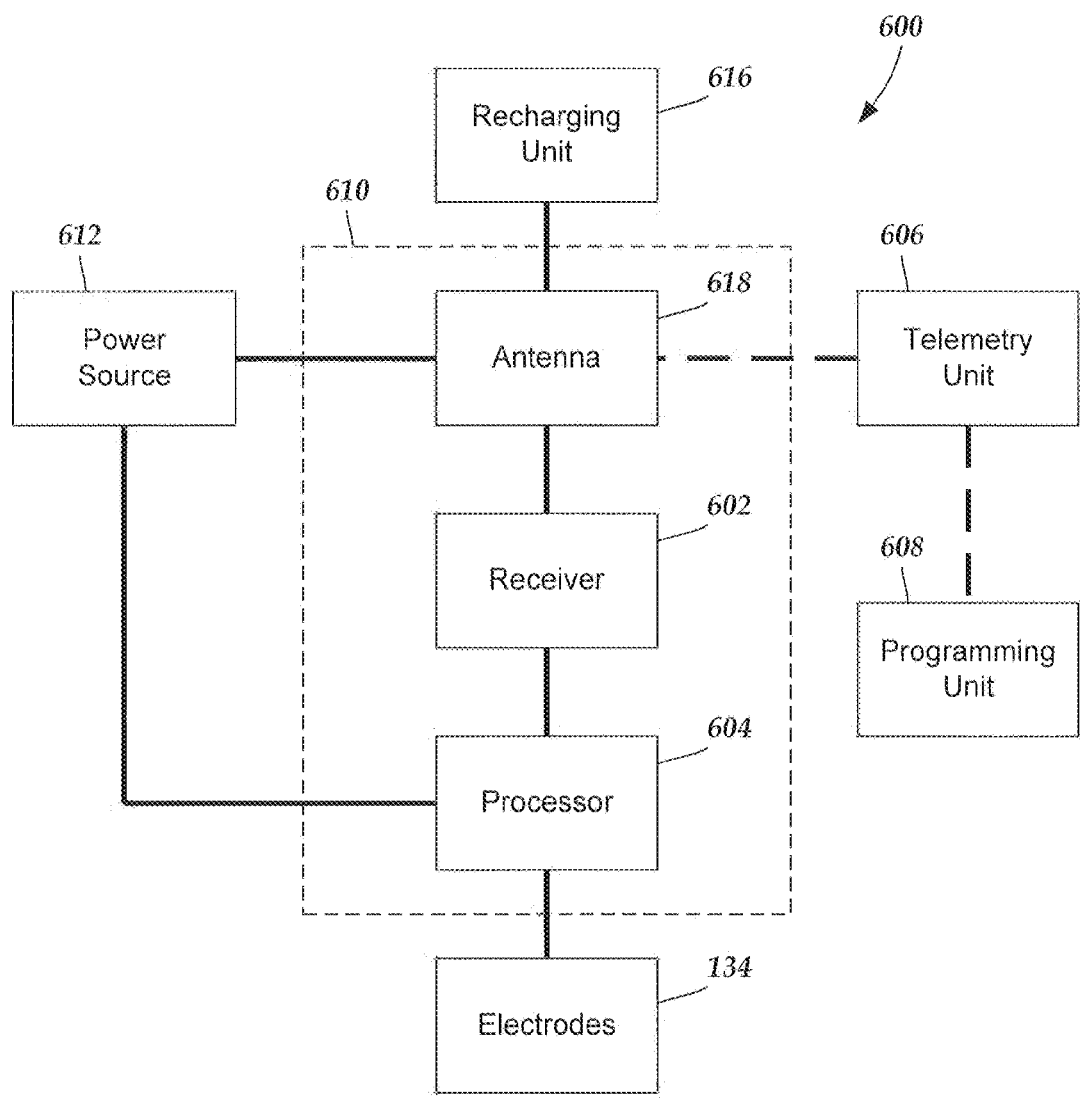
FIG. 6 is a schematic overview of one embodiment of components of a stimulation system, including an electronic subassembly disposed within a control module, according to the invention.

FIG. 6 is a schematic overview of one embodiment of components of an electrical stimulation system 600 including an electronic subassembly 610 disposed within a control module. It will be understood that the electrical stimulation system can include more, fewer, or different components and can have a variety of different configurations including those configurations disclosed in the stimulator references cited herein.

Some of the components (for example, a power source 612, an antenna 618, a receiver 602, and a processor 604) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical. resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193 incorporated herein by reference.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment electrical current is emitted by the electrodes 134 on the paddle or lead body to stimulate nerve fibers, muscle fibers, or other body tissues near the electrical stimulation system. The processor 604 is generally included to control the timing and electrical characteristics of the electrical stimulation system. For example, the processor 604 can, if desired, control one or more of the timing, frequency, strength, duration, and waveform of the pulses. In addition, the processor 604 can select which electrodes can be used to provide stimulation, if desired. In some embodiments, the processor 604 selects which electrode(s) ate cathodes and which electrode(s) are anodes. In some embodiments, the processor 604 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (e.g., RF signals) from an external telemetry unit 606 which is programmed by the programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and the receiver 602 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 600 to cease operation, to start operation, to start charging the battery, or to stop charging the battery. In other embodiments, the stimulation system docs not include the antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead, comprising:
   a lead body having a proximal end portion, a distal end portion, a distal tip, and a longitudinal length;
   a plurality of electrodes disposed along the distal end portion of the lead body, the plurality of electrodes comprising a tip electrode disposed on the distal tip of the lead body, the tip electrode comprising
      an electrode body having an outer stimulating surface, a proximal end, a closed distal end, a circumference, and a longitudinal length, and
      an internal lumen defined in the electrode body and extending inwardly from an opening in the proximal end of the electrode body, the internal lumen defining a plurality of longitudinal grooves formed along the internal lumen and extending deeper into the electrode body than adjacent portions of the internal lumen, each of the plurality of longitudinal grooves extending along the internal lumen in a direction that is parallel to the longitudinal length of the electrode body,
      wherein a portion of the lead body is disposed within the internal lumen and into the plurality of longitudinal grooves through the opening in tire proximal end of the electrode body, wherein the portion of the lead body within the internal lumen and the plurality of longitudinal grooves facilitates retention of the tip electrode on the distal tip of the lead body;
   a plurality of terminals disposed along the proximal end portion of the lead body; and
   a plurality of conductors, each conductor of the plurality of conductors electrically coupling each of the plurality of terminals to at least one of the plurality of electrodes.

2. The implantable electrical stimulation lead of claim 1, wherein at least one of the plurality of longitudinal grooves extends from the opening in the proximal end of the internal lumen.

3. The implantable electrical stimulation lead of claim 1, wherein the plurality of longitudinal grooves each extend along at least 50% of the longitudinal length of the electrode body.

4. The implantable electrical stimulation lead of claim 1, wherein the tip electrode is isodiametric with the lead body.

5. The implantable electrical stimulation lead of claim 1, wherein the tip electrode further comprises a channel defined in the internal lumen, the channel extending deeper into the electrode body than adjacent portions of the internal lumen, the channel extending along at least 25% of the circumference of the electrode body.

6. The implantable electrical stimulation lead of claim 5, wherein the channel extends around the entire circumference of the electrode body.

7. The implantable electrical stimulation lead of claim 5, wherein the channel intersects at least a portion of at least one of the plurality of longitudinal grooves.

\* \* \* \* \*